(12) United States Patent
Wilson, Jr. et al.

(10) Patent No.: US 7,293,654 B1
(45) Date of Patent: Nov. 13, 2007

(54) FLEXIBLE MEDICAL SUPPLIES PACKAGING FOR CONVENIENCE KITS

(75) Inventors: Bruce H. Wilson, Jr., Madison, CT (US); Philip Justin Hamrock, Branford, CT (US); Joan Marie Lang, Branford, CT (US); Steven D. Kimmell, Granada Hills, CA (US); Gregory Robert Art, Monument, CO (US)

(73) Assignee: Aplicare, Inc., Meriden, CT (US)

( * ) Notice: Subject to any disclaimer, the term of this patent is extended or adjusted under 35 U.S.C. 154(b) by 303 days.

(21) Appl. No.: 10/904,951

(22) Filed: Dec. 7, 2004

(51) Int. Cl.
*B65D 69/00* (2006.01)
*A61B 19/08* (2006.01)

(52) U.S. Cl. ............... 206/572; 206/363; 206/525.1; 128/852

(58) Field of Classification Search ........... 206/234, 206/438, 570–572, 363–366, 525.1, 484; 128/849, 852, 855; 383/38–40, 109, 110, 383/113, 123
See application file for complete search history.

(56) References Cited

U.S. PATENT DOCUMENTS

| | | | | |
|---|---|---|---|---|
| 3,187,903 A | * | 6/1965 | Oltz | 383/38 |
| 3,650,393 A | * | 3/1972 | Reiss et al. | 206/571 |
| 3,889,667 A | * | 6/1975 | Collins | 128/855 |
| 3,981,398 A | | 9/1976 | Bushoff | 206/223 |
| 4,170,300 A | | 10/1979 | Pick | 206/365 |
| 4,197,941 A | | 4/1980 | Halasz | 206/216 |
| 4,213,598 A | | 7/1980 | Halasz | 206/45.14 |
| 4,522,302 A | | 6/1985 | Paikoff | 206/570 |
| 4,523,679 A | | 6/1985 | Paikoff et al. | 206/370 |
| 4,595,102 A | | 6/1986 | Cianci et al. | 206/572 |
| 4,720,017 A | | 1/1988 | Pestes | 215/227 |
| 4,828,113 A | | 5/1989 | Friedland et al. | 206/570 |
| 4,928,830 A | | 5/1990 | Brewer | 206/570 |
| 4,949,843 A | * | 8/1990 | Stokes | 383/38 |
| 5,022,521 A | | 6/1991 | Kane | 206/370 |
| 5,059,271 A | * | 10/1991 | Taub | 128/849 |
| 5,117,981 A | | 6/1992 | Crawford et al. | 206/570 |
| 5,143,210 A | | 9/1992 | Warwick et al. | 206/45.13 |
| 5,170,804 A | * | 12/1992 | Glassman | 128/849 |
| 5,222,600 A | | 6/1993 | Stoddard et al. | 206/370 |
| 5,718,245 A | | 2/1998 | Horn | 128/897 |
| 5,766,715 A | | 6/1998 | Garconnet | 428/40.1 |
| 5,862,916 A | | 1/1999 | Utecht | 206/570 |
| 5,931,303 A | * | 8/1999 | Salvadori | 206/570 |
| 5,947,296 A | | 9/1999 | Castora | 206/571 |
| 5,979,658 A | | 11/1999 | Allen et al. | 206/572 |
| 5,988,172 A | * | 11/1999 | Sosebee | 128/849 |
| 6,012,586 A | | 1/2000 | Misra | 206/571 |
| 6,102,205 A | | 8/2000 | Greff et al. | 206/438 |
| 6,291,171 B1 | | 9/2001 | Ricciardi et al. | 435/6 |
| 6,412,639 B1 | | 7/2002 | Hickey | 206/570 |
| 6,502,699 B1 | | 1/2003 | Watson | 206/571 |

\* cited by examiner

*Primary Examiner*—Luan K Bui
(74) *Attorney, Agent, or Firm*—Dinsmore & Shohl LLP; Monika J. Hussell

(57) ABSTRACT

A sterile, compact packaging is provided to present components in order of preferred or required use in a medical procedure. Pockets are arranged along one or more endsections of the packaging, and an absorbent material is at least partially adhered to the moisture proof sheet at a workspace thereon. Components are placed in the pockets in order of use, and the packaging is folded up. The folded packaging is sealed in a gas-permeable pouch, which maintains the components in a sterile condition until use. In use, the packaging is unfolded to expose the medical components.

2 Claims, 8 Drawing Sheets

FLEXIBLE MEDICAL SUPPLIES PACKAGING FOR CONVENIENCE KITS

BACKGROUND OF INVENTION

The present invention is directed toward a flexible, compact and disposable packaging for a convenience kit of medical supplies for use in medical procedures (e.g., central line dressing change, VAD access, wound care and laceration repair).

DETAILED DESCRIPTION

Figure 1:
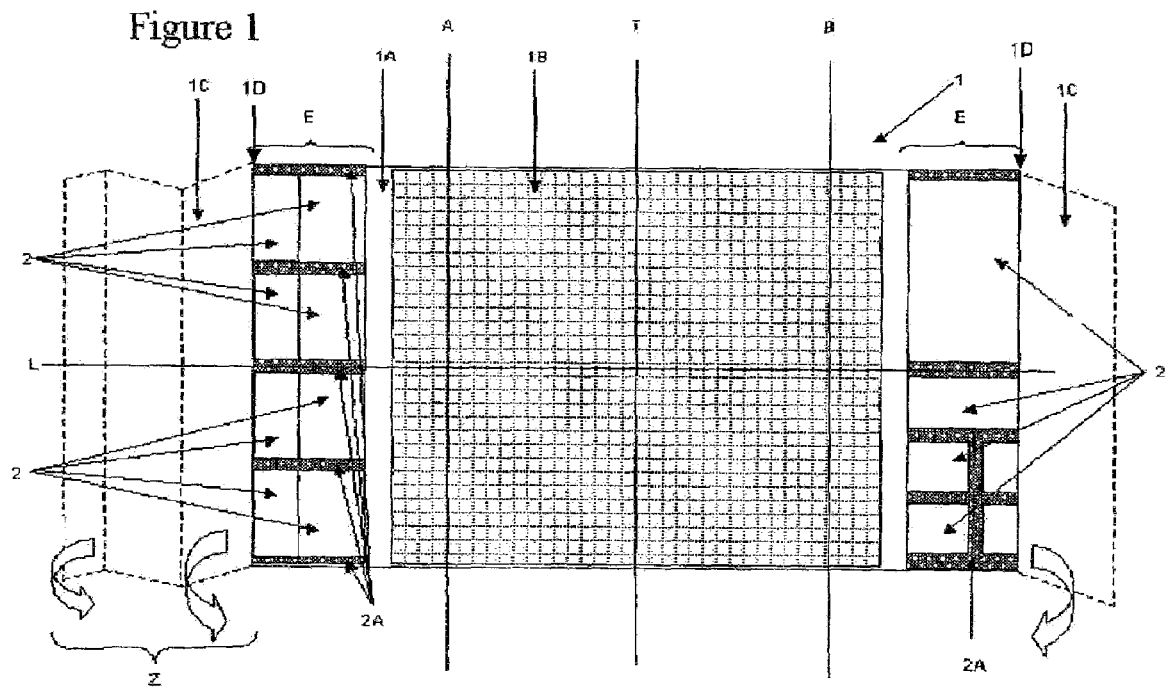
FIG. 1 is a view of an embodiment of the packaging of the present invention.
Figure 2:
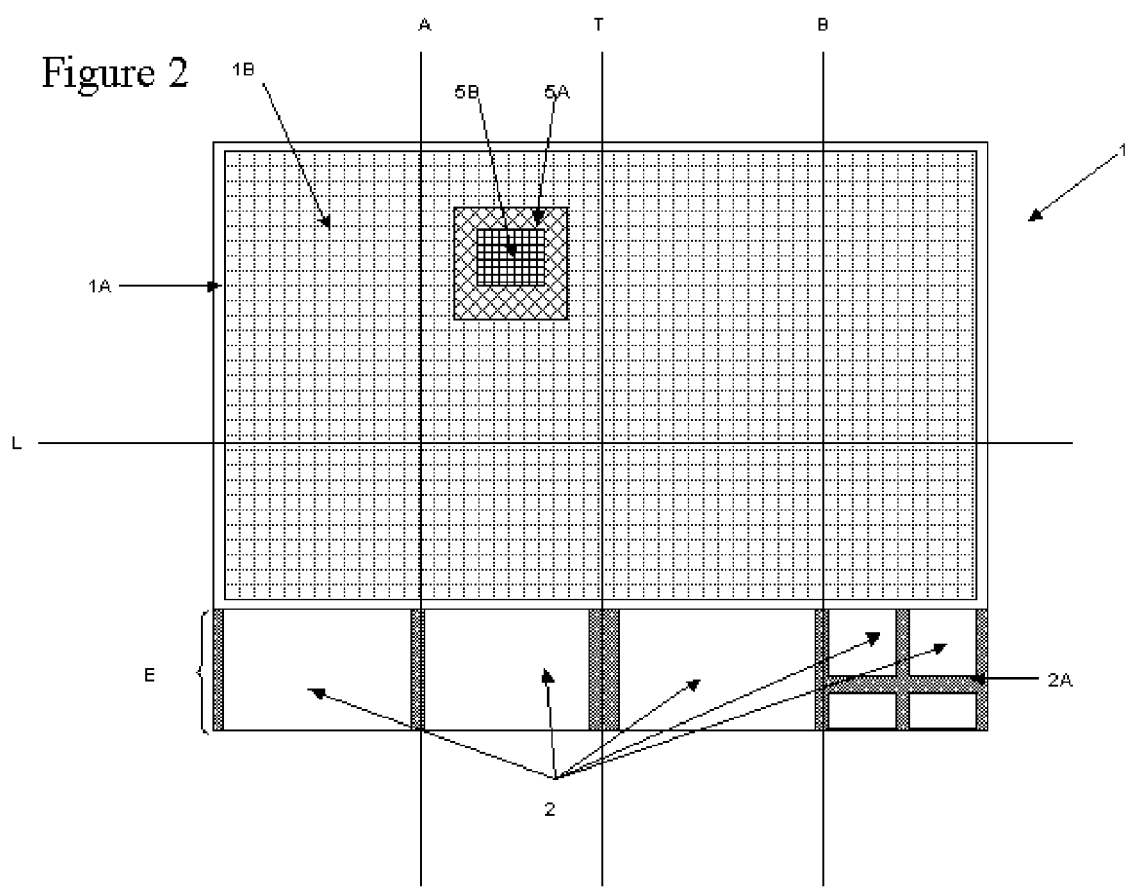
FIG. 2 is a view of another embodiment of the packaging of the present invention.

Referring now to FIGS. 1 and 2, the packaging of the present invention comprises a sheet 1 of one or more materials, sufficiently flexible to permit folding of the same in accordance with the present invention, and having a moisture proof exterior 1A which forms a barrier to contamination to or from the surface upon which the packaging is placed. The moisture proof exterior 1A may comprise polyethylene, polypropylene, or other plastic sheeting, foil laminate, plastic impregnated paper or other material sufficient to prevent liquid and/or moisture from migrating through the sheet 1. In some uses of the packaging of the present invention, it may be beneficial for the moisture proof exterior 1A to have a tacky surface so as to prevent the packaging itself from slipping off of or moving on a smooth surface. Such a tacky surface may be realized by removing the slip chemical additive from the plastic formulation used to develop the exterior layer; or by adding a tacky coating of latex or varnish, or other adhesive material, to the exterior surface of the exterior material 1A. The longitudinal axis of the sheet 1 is referenced in the figures by the letter L, and the transverse axis perpendicular to the longitudinal axis is referenced by the letter T.

At least one pocket 2 is affixed to or formed on the sheet 1, at one or more of its endsections (referenced by the letter E in FIGS. 1 and 2), to hold medical supplies desirable in the performance of a medical procedure. The pockets 2 may be formed on sheet 1 by adhering one or more second layers to sheet 1 or, as depicted in FIG. 1, one or more of the edges 1C of sheet 1 may be folded back onto sheet 1, and partially adhered thereto to form pocket(s) 2, endsections E and new sheet edges 1D. The pockets so formed inherently have pocket openings located on the side opposite the corresponding sheet edge 1D, opening towards the workspace 1B. The adhesions forming the sides of the pockets 2 may be made by means of heat sealing, adhesive bonding, RF or sonic welding, or stitching, or other means known in the art, and are referenced in the figures as 2A.

Multiple layered pockets 2 may be formed at the endsections E, by adhering a second layer to a first row pocket 2, or by folding edges 1C of sheet 1 back onto sheet 1 in a z-fold, as depicted on FIG. 1 and referenced by the letter Z.

The pockets 2 may be individually sized to receive, permit insertion of and retain specific medical supplies, depending on the procedure for which a kit is intended, and the pockets may be positioned on sheet 1 such that the intended medical supplies are secured by the pockets 2 in an order of preferred or required use. The pockets 2 should be positioned on sheet 1 to permit the folding of sheet 1 as hereinafter described.

The non-pocketed portion of the sheet 1 forms a workspace, at least partially covered by a sterile layer of absorbent material 1B, replacing the need for, and acting as, a separate sterile towel or drape. The absorbent material 1B may comprise an absorbent, pliable material such as paper or other fiber based engineered material, or other material capable of retaining fluids and moisture associated with the medical procedure, deterring pooling or running of such fluids, and/or providing a non-slippery surface so that components placed or dropped thereon do not easily slide off. The absorbent material 1B is at least partially adhered to the sheet 1.

Figure 3:
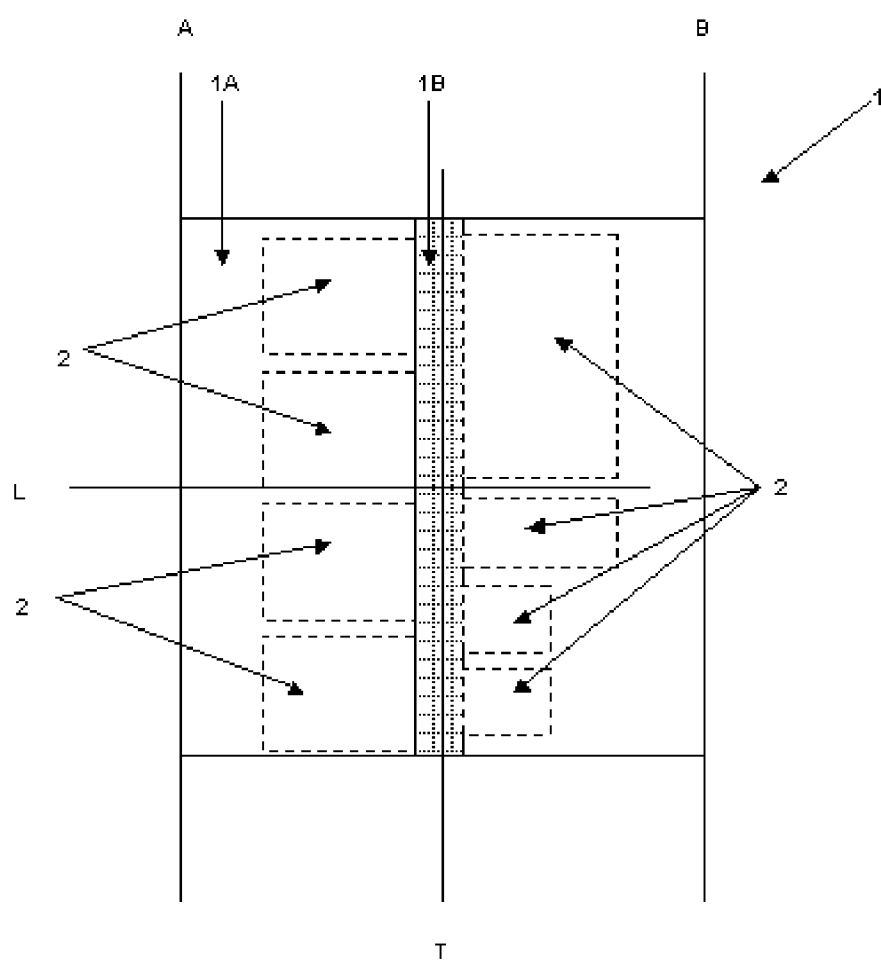
FIGS. 3 and 4 show the packaging of FIG. 1, as successively folded in accordance with an embodiment of the present invention.
Figure 4:
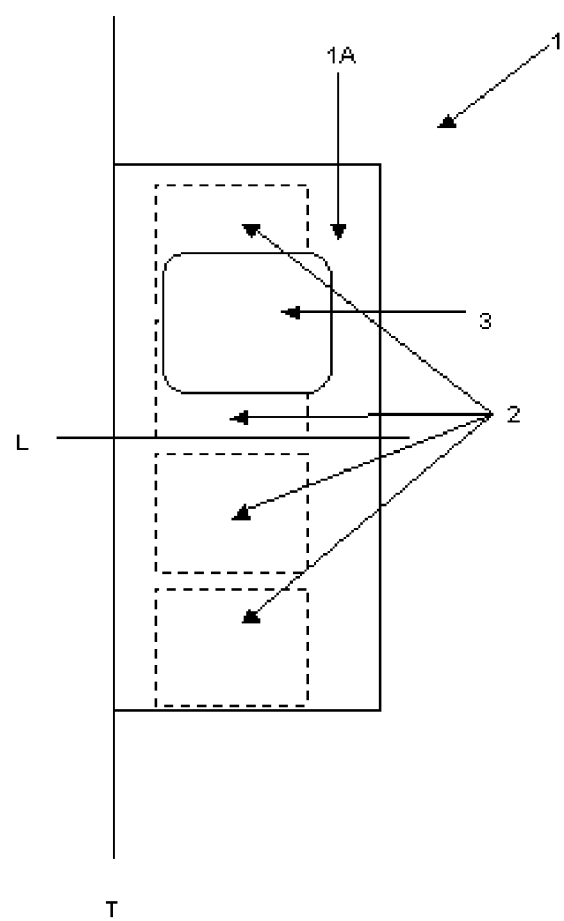
Figure 5:
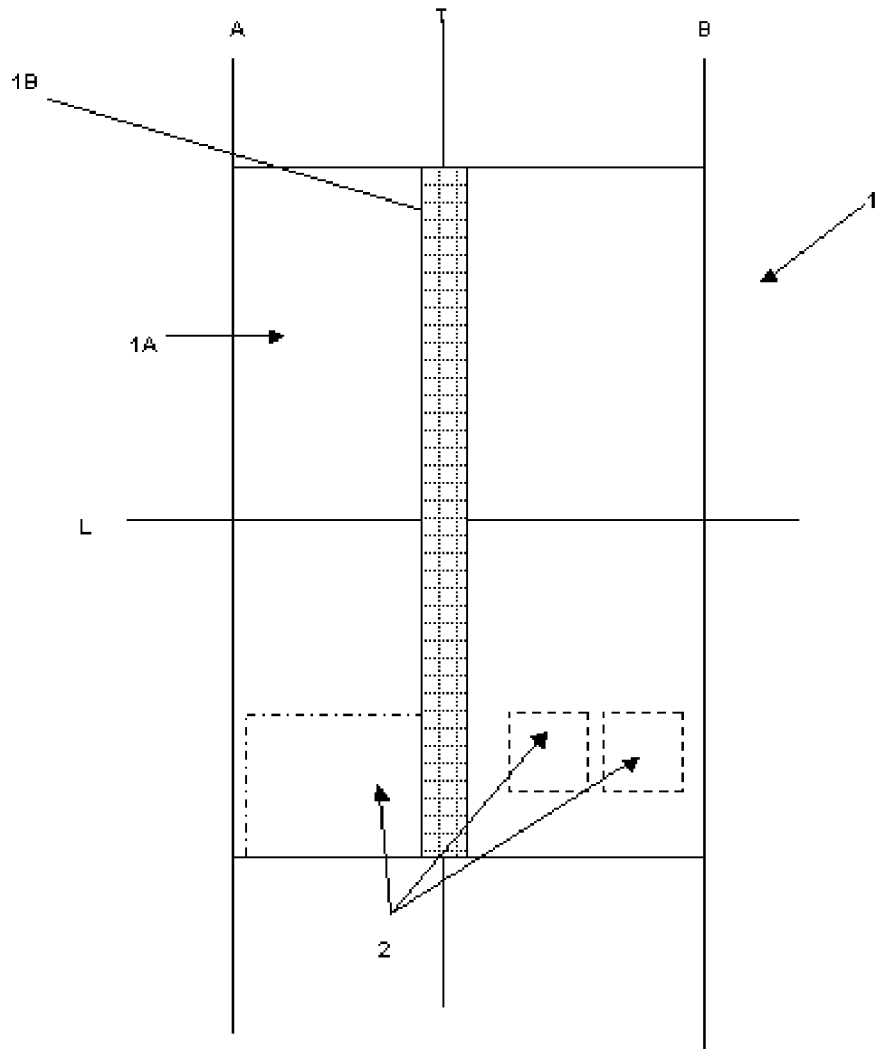
FIGS. 5 and 6 show the packaging of FIG. 2, as successively folded in accordance with an embodiment of the present invention.
Figure 6:
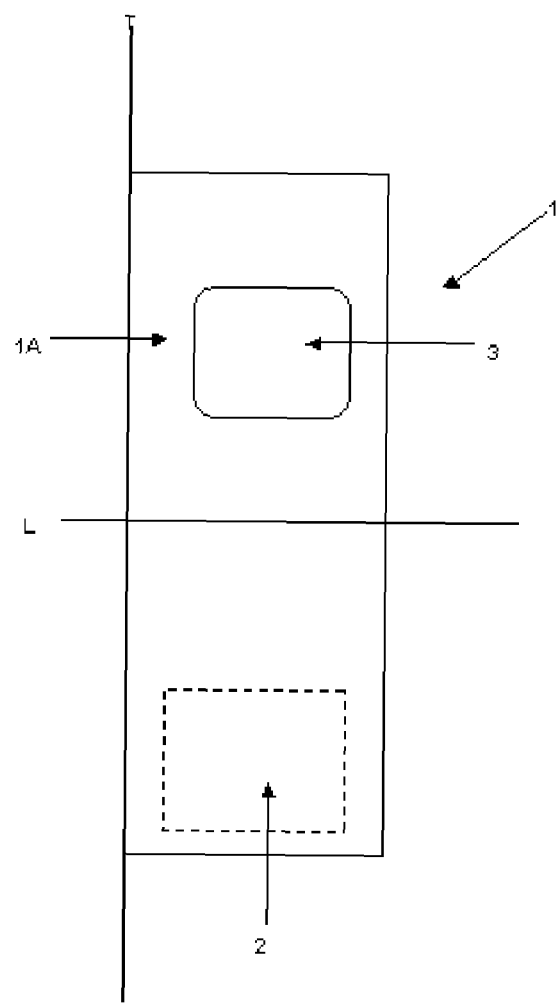
Figure 7:
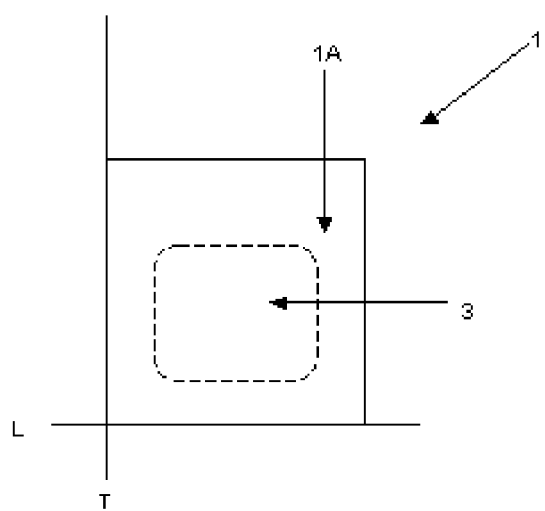
FIG. 7 shows the packaging of FIGS. 1 and 2, as further folded in accordance with an embodiment of the present invention.

As depicted in FIGS. 3-7, the sheet 1 of the present invention is capable of being folded to form a package which would securely hold medical supplies contained in pockets 2 thereof. The method of folding sheet 1 may comprises a first and second fold along reference lines A and B of sheet 1, respectively, towards the transverse axis T of the sheet 1 (as depicted in FIGS. 3 and 5); a third fold may be made along or near the transverse axis T of sheet 1 (as depicted in FIGS. 4 and 6); and a fourth fold may be made along or near the longitudinal axis L of sheet 1 (as depicted in FIG. 7), thereby compactly and securely holding the medical supplies stored within the pockets 2.

In assembly of the packaging of the present invention, medical supplies necessary to complete a medical procedure (e.g., antiseptic hand cleaners, swab sticks, gauze, tape, protective dressings, towels, band aids, cauteries, sponges, dressings, instruments, IV tubing, measuring tape, needles and syringes, non-adherent pads, pop up cup, skin protectant products, small drapes, stopcocks, sutures, tourniquets, etc.) are placed in the pockets 2 affixed to or formed by sheet 1 of the packaging of the present invention, in order of their preferred or required use. In certain procedures it may be beneficial to place a gauze pad 5A and/or a non-adhering pad 5B in the kit, free from any pockets, as shown in FIG. 2. Further, as depicted in FIGS. 5 and 6, certain infection control supplies 3 (e.g., gloves and face mask) may be placed in the kit after the third fold, which allows the user to open the packaging by unfolding the last fold(s), depending on the placement of the supplies 3, put on the infection control supplies 3, and then aseptically open the remaining fold(s) of sheet 1 without contaminating the sterile components contained therein or the absorbent material 1B/workspace of sheet 1. Upon opening of the packaging, the sterile absorbent material 1B is automatically presented as needed without further action of the user or risk of contamination.

Figure 8:
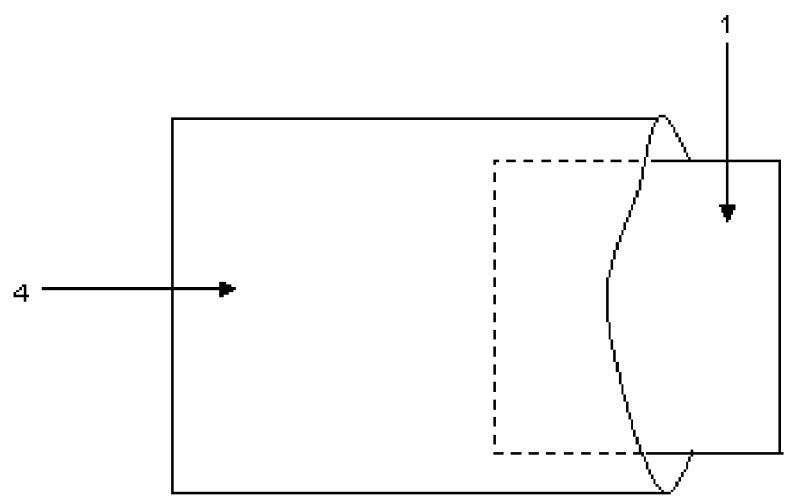
FIG. 8 shows the packaging of FIGS. 1 and 2 being inserted into a pouch as contemplated by an embodiment of the present invention.

In a further embodiment of the present invention, as depicted in FIG. 8, the folded package is inserted into a sealable, gas-permeable, moisture resistant pouch 4, preferably sealed opposite to the last fold thereof such that when the pouch is opened at the end opposite the sealed end, the kit will be most likely to drop on a work surface on the last fold.

The pouch 4 and the medical supplies contained in the kit are sterilized based upon known means of sterilization, including but not limited to gas and radiation, known to those skilled in packaging medical supplies. The pouch 4 may further be used as a convenient vehicle for gathering and disposing of used medical supplies and sheet 1 once the procedure has been completed.

Thus, a flexible medical supplies packaging for a convenience kit is provided. One skilled in the art will appreciate that the present invention can be practiced by other than the described embodiments, which are presented for purposes of illustration and not limitation, and the present invention is limited only by the claims that follow.

What is claimed is:

1. A kit for a medical procedure, the kit comprising:
    a plurality of medical supplies, and
    a packaging comprising:
        a flexible sheet having a moisture proof exterior, the sheet having a generally rectangular configuration defining a longitudinal axis and a transverse axis, having edges, at least one endsection, and a workspace,
        the sheet further having a plurality of pockets arranged on an endsection of said sheet, the pockets formed by folding an edge of the sheet back onto the sheet, and being adhered to the said sheet along seam lines to define pocket perimeters, so that said pockets are individually sized to permit insertion and retain one or more of the medical supplies, and
        the sheet having an absorbent cloth, substantially covering the sheet at the workspace of the sheet,
        wherein the packaging is folded up first to the transverse axis, then along the transverse axis, and then along the longitudinal axis; and
    wherein the plurality of medical supplies are disposed in the pockets of the packaging, in order of use.

2. The kit of claim 1, further comprising a sealable pouch disposed over the folded packaging.

* * * * *